United States Patent [19]

Wallach, deceased et al.

[11] Patent Number: 4,590,187

[45] Date of Patent: May 20, 1986

[54] PHOSPHOLIPASE A$_2$ INHIBITION USING 4,1-BENZOXAZEPINE-2-(3H)-ONES

[75] Inventors: Donald P. Wallach, deceased, late of Richland, Mich., by Vera Wallach, legal representative; Donald E. Ayer; Jacob Szmuszkovicz, both of Kalamazoo, Mich.

[73] Assignee: The Upjohn Company, Kalamazoo, Mich.

[21] Appl. No.: 683,539

[22] Filed: Dec. 19, 1984

Related U.S. Application Data

[63] Continuation-in-part of Ser. No. 552,996, Nov. 17, 1983, abandoned, and Ser. No. 552,997, Nov. 17, 1983, abandoned.

[51] Int. Cl.$^4$ ............... A61K 31/55; C07D 267/14
[52] U.S. Cl. ............... 514/211; 260/239.3 B
[58] Field of Search ............... 260/239.3 B; 514/211

[56] References Cited

U.S. PATENT DOCUMENTS

| | | | |
|---|---|---|---|
| 3,122,554 | 2/1984 | Poos | 260/239.3 |
| 3,346,565 | 10/1967 | Testa et al. | 260/239.3 |
| 3,598,808 | 8/1971 | Szmuszkovicz | 260/239.3 |
| 4,297,280 | 10/1981 | Hirai et al. | 260/245.5 |
| 4,307,091 | 12/1981 | Brown et al. | 424/248.4 |
| 4,341,704 | 7/1982 | Hirai et al. | 260/243.3 |

FOREIGN PATENT DOCUMENTS

| | | | |
|---|---|---|---|
| 2949773 | 6/1980 | Fed. Rep. of Germany | 260/239.3 B |
| 2480751 | 10/1981 | France | 260/239.3 B |

OTHER PUBLICATIONS

Chemical Abstracts, vol. 63, cols. 18088–18089 (1965), abstracting Testa et al. in "Farmaco" (Pavia) (Ed. Sci.), vol. 20, No. 5, pp. 323–335 (1965).
Derwent Farmdoc 27355E and 25429C.

*Primary Examiner*—Robert T. Bond
*Attorney, Agent, or Firm*—Lawrence T. Welch

[57] ABSTRACT

The present invention provides certain novel 4,1-benzoxazepin-2(3H)-ones which are useful as inhibitors of phospholipase A$_2$ and thus as inhibitors of arachidonate mobilization. These compounds are thus useful whenever it is medically necessary or desirable to inhibit the biosynthesis of the products of the arachidonic acid cascade.

10 Claims, No Drawings

PHOSPHOLIPASE A₂ INHIBITION USING 4,1-BENZOXAZEPINE-2-(3H)-ONES

CROSS REFERENCE TO RELATED APPLICATIONS

This application is a continuation-in-part of applications Ser. Nos. 552,996 and 552,997, both filed Nov. 17, 1983, both now abandoned.

BACKGROUND OF THE INVENTION

The present invention relates to novel compositions of matter. These novel compositions are to be used in the treatment of conditions or symptoms due to certain disease conditions in mammals. In particular this invention relates to novel compounds which are useful in inhibiting the formation of products of the "aracidonic acid cascade" in such pathological states. This inhibition is accomplished by inhibiting the action of the enzyme phospholipase $A_2$, an important mediator in the cascade, by administering certain novel 4,1-benzoxazepin-2(3H)-ones.

The important role of phospholipase $A_2$ in mammalian metabolism through the formation of prostaglandins is now well known. See W. Vogt, Advances in Prostaglandins and Thromboxane Research, Vol. 3, page 89 (1978); P. C. Isakson, et al., Advances in Prostaglandin and Thromboxane Research, Vol. 3, page 113, (1978). Phospholipase $A_2$ is responsible for the hydrolysis of arachidonic acid-containing phospholipids, thereby providing substrate for the multiple enzymes of the arachidonic acid cascade.

The products of the arachidonic acid cascade are varied. These products include prostaglandins, thromboxanes, leukotrienes, and other hydroxylated derivatives of arachidonic acid, which are referred to as "eicosanoids." While generally the products of the cascade are beneficial, in certain disease processes and other conditions the excessive production of eicosanoids induces deleterious consequences such as inflammation (see paper by N. A. Plummer, et al.; abstracted in Journal of Investigative Dermatology, Vol. 68, No. 4, p. 246 (1977)); erythema (N. A. Plummer, supra); platelet aggregation (B. B. Vargaftig, J. Pharm. Pharmacol., Vol. 29, p. 222–228 (1977)); and the release of SRS-A (slow reacting substance-anaphylaxis), a known mediator of allergenic responses. The inhibition of phospholipase $A_2$ prevents these and similar conditions mediated by the action of this enzyme.

Some inhibitors of phospholipase $A_2$ are known. R. J. Flower and G. J. Blackwell have shown that certain anti-inflammatory steroids induce biosynthesis of a phospholipase $A_2$ inhibitor which prevents prostaglandin generation. See Nature, Vol. 278, p. 456 (1979). These steroids are not direct inhibitors of phospholipase $A_2$, but rather stimulate the synthesis of a phospholipase inhibiting factor called lipocortin, lipomodulin, or macrocortin.

Some examples of direct phospholipase $A_2$ inhibition are known. Indomethacin, a drug with anti-inflammatory properties, has been shown to inhibit at least one phospholipase $A_2$ enzyme. See K. L. Kaplan, et al., Proc. Natl. Acad. Sci., Vol. 75, No. 6, pp. 2955–2988 (1978). The compound has been shown to inhibit phospholipase $A_2$ enzymes, isolated respectively from the venoms of Russel Viper, *Crotalus adamanteus*, and bee, and from pig pancreas. Certain local anesthetics have been shown to inhibit phospholipase $A_2$ activity by competing with calcium ion, which appears to be a requirement for phospholipase activity. See W. Vogt, Advances in Prostaglandin and Thromboxane Research, Vol. 3 p. 89 (1978). Bromphenacyl bromide has been shown to inhibit phospholipase $A_2$ by acylating a histidine residue which is the active site of the molecule. See M. Roberts, et al., Journal of Biological Chemistry, Vol. 252, pp. 2405–2411 (1977). R. Blackwell, et al., in British Journal of Pharmacy, Vol. 62, p. 79–89 (1978) has disclosed that mepacrine inhibits the activity of phospholipase $A_2$ derived from perfused guinea pig lung. Certain butyrophenones are disclosed as phospholipase $A_2$ inhibitors in U.S. Pat. No. 4,239,780.

PRIOR ART

U.S. Pat. No. 3,122,554 discloses certain 1,5-dihydro-5-phenyl-4,1-benzoxazepin-2(3H)-ones which are optionally substituted at the nitrogen by a lower alkyl group. These compounds are stated to be useful as central nervous system depressants, as tranquilizers, and as muscle relaxants. Similarly, U.S. Pat. No. 3,346,565 discloses certain 1,2,3,5-tetrahydro- and 3,5-dihydro-4,1-benzoxazepines having alkyl, aralkyl, acyl, and amine substituents on the nitrogen. These compounds are stated to be useful as sedatives, tranquilizers, and hypnotics. Derwent Farmdoc 27355E, abstracting Japanese application No. 35576/82 (J5 7035-576) discloses certain 4,1-benzoxazepine-3-acetic acid derivatives which are stated to be useful as minor tranquilizers. U.S. Pat. No. 4,307,091 discloses certain 4H-1,4-benzoxazin-2,3-diones which are stated to be useful as antiallergic agents. Derwent Farmdoc 25429C, which abstracts Belgian application No. 880,282, discloses certain 4,1-benzoxazepine derivatives which are stated to be useful as CNS depressants. U.S. Pat. No. 3,598,808 discloses certain perhydro-5-substituted-phenyl-cycloalkapolyene-4,1-oxazepines as useful in the treatment of respiratory disorders, e.g., asthma. U.S. Pat. Nos. 4,341,704 and 4,297,280 disclose certain 4,1-benzoxazepines having ($C_7$–$C_9$)aralkyl substituents on the nitrogen. These compounds are stated to be useful as antidepressants. U.S. Pat. No. 3,346,565 discloses certain 4,1-benzoxazepin-2(3H)-ones having sedative, tranquilizing, and antidepressant activity.

SUMMARY OF THE INVENTION

The present invention particularly provides a compound of the Formula I wherein $R_1$ is
  (a) cyclopropylmethyl,
  (b) 2-phenylethyl,
  (c) $-(CH_2)_n-NR_4R_5$, or
  (d) $-CH_2-CH_2-(CH_2)_m-R_{11}$,
wherein $R_{11}$ is
  (a) $-O-PhX$,
  (b) $-S(O)_p-PhX$,
  (c) $-O-Z$,
  (d) $-PhX$,
  (e) $-OR_2$, or
  (f) phthalimido;
wherein PhX is
  (a) phenyl, or
  (b) phenyl substituted by $X_1$;
wherein $X_1$ is
  (a) chloro
  (b) bromo,
  (c) fluoro, (d) nitro,
(e) trifluoromethyl,
(f) methoxy,
(g) hydroxy,
(h) $(C_1-C_3)$alkyl,
(i) —$SCH_3$, or
(j) —$CO_2M$, wherein M is hydrogen, $(C_1-C_3)$alkyl, or a pharmacologically acceptable cation; wherein n is 2 or 3, wherein m is an integer from zero to 4, inclusive, with the proviso that m is not zero when $R_{11}$ is phenyl; wherein p is an integer from zero to 2, inclusive, and wherein $R_4$ and $R_5$ are the same or different and are $(C_1-C_3)$ alkyl or $R_4$ amd $R_5$ together with the nitrogen atom to which they are attached form 1-azetidinyl, 1-pyrrolidinyl, 1-piperidinyl, or 4-morpholinyl; wherein $R_2$ is
  (a) hydrogen,
  (b) $(C_1-C_2)$alkyl, or
  (c) phenyl;
wherein Z is $(C_3-C_6)$cycloalkyl; wherein $Y_1$ is
  (a) hydrogen,
  (b) chloro,
  (c) bromo,
  (d) fluoro,
  (e) nitro, or
  (f) trifluoromethyl,
including the acid addition salts thereof when $R_1$ is —$(CH_2)_n$—$NR_4R_5$; with the following provisos:
  (1) when $R_1$ is cyclopropylmethyl and $R_2$ is methyl or when $R_1$ is —$CH_2$—$CH_2$—$(CH_2)_m$—$R_{11}$, $Y_1$ is not hydrogen;
  (2) when $R_1$ is cyclopropylmethyl, 2-phenylethyl, or —$(CH_2)_n$—$NR_4R_5$, $Y_1$ is not nitro;
  (3) $R_2$ is hydrogen or $(C_2-C_3)$alkyl only when $R_1$ is —$CH_2$—$CH_2$—$(CH_2)_m$—$R_{11}$.

The carbon atom content of various hydrocarbon-containing moieties is indicated by a prefix designating the minimum and maximum number of carbon atoms in the moiety, i.e., the prefix $(C_i-C_j)$ indicates a moiety of the integer "i" to the integer "j" carbon atoms, inclusive. Thus $(C_1-C_3)$alkyl refers to alkyl of one to 3 carbon atoms, inclusive, or methyl, ethyl, propyl, and isopropyl.

Examples of cycloalkyl of 3 to 6 carbon atoms, inclusive, are cyclopropyl, cyclobutyl, cyclopentyl, and cyclohexyl.

Examples of substituted phenyl within the scope of PhX are p-chlorophenyl, m-chlorophenyl, p-tolyl, m-tolyl, o-tolyl, p-ethylphenyl, 5-methylphenyl, 4-bromophenyl, and the like.

Phthalimido means 1,3-dihydro-1,3-dioxo-2H-isoindol-2-yl.

The compounds of the present invention may be in the form of pharmacologically acceptable salts. These salts are formed when M is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
1-methylpiperidine,
4-ethylmorpholine,
1-isopropylpyrrolidine,
2-methylpyrrolidine,
1,4-dimethylpiperazine,
2-methylpiperidine,
and the like, as well as amines containing water-solubilizing or hydrophilic groups, e.g.,
mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
glactamine,
N-methylglycamine,
N-methylglucosamine,
ephedrine,
phenylephrine,
epinephrine,
procaine,
and the like. Further useful amine salts are the basic amino acid salts, e.g.,
lysine and
arginine.

Examples of suitable pharmacologically acceptable quaternary ammonium cations are
tetramethylammonium,
tetraethylammonium,
benzyltrimethylammonium,
phenyltriethylammonium, and the like.

Compounds of the present invention have been tested in standard laboratory tests to evaluate their ability to inhibit phospholipase $A_2$. In the perfused guinea pig lung, 1-(3-phenoxypropyl)-7-chloro-1,5-dihydro-5-methyl-5-phenyl-4,1-benzoxazepine-2(3H)-one (Example 2) has been shown to be preferred, exhibiting complete inhibition of the enzyme at $1.8 \times 10^{-6}$ Molar.

Thus, the compounds of the present invention are useful whenever it is medically necessary or desirable to inhibit phospholipase $A_2$ in a mammalian system. They are particularly useful in treating symptoms or conditions resulting from the action of the arachidonic acid cascade.

The symptoms or conditions treated or prevented by the compounds of this invention are those which are produced as a result of the excessive stimulation of the arachidonic acid cascade during certain disease processes or conditions. The multiple enzymes of the cascade act upon 5,8,11,14-eicosotetraenoic acid to produce prostaglandins, leukotrienes, and hydroxylated derivatives. At certain times during these disease processes or conditions, some of these products are responsible for the symptoms or conditions noted above, e.g., inflammation, erythema, allergic responses, and similar conditions. Phospholipase $A_2$ provides the substrate for these enzymes of the cascade by hydrolysis of arachidonate rich phospholipids. Thus, phospholipase $A_2$ is an important mediator in these conditions. Inhibition of this enzyme by the method of this invention is thus effective to treat or prevent the symptoms or conditions, which are designated as PMC's (phospholipase $A_2$ mediated conditions).

The precise mechanisms of the disease processes or conditions which stimulate the arachidonic acid cascade are not clearly understood. The essential prerequisite, however, is enhanced activity of the phospholipases which provide arachidonate to the series of reactions designated as the arachidonic acid cascade. The method of this invention is simply to block the action of the phospholipases and cut off the flow of arachidonate into the cascade, irrespective of the stimulus or stimuli which may be present. This is accomplished with the compounds of the present invention. Thus, the method of this invention is suitable for treating seemingly unrelated diseases whose common element is the stimulation of the arachidonic acid cascade. The term "phospholipase $A_2$ mediated conditions" (PMC) includes all untoward conditions or symptoms which are the result of the excessive stimulation of the arachidonic acid cascade. These conditions encompass allergenic diseases, inflammatory conditions (including chronic inflammatory conditions such as rheumatoid arthritis), burns, and hypoxic conditions at the cellular level such as coronary infarcts, or infarcts of other tissues. In these latter infarct conditions it is desirable to block phospholipase activity to prevent the destruction of phospholipids which are substrates for phospholipases, and are integral structural components of cellular membranes.

The method of this invention could be used on any mammal whose metabolic system includes the phospholipase induced arachidonic acid cascade. The mammals which are preferred are generally domesticated animals and humans. Humans are the most preferred mammals to be treated by the method of this invention.

The degradation of cell membranes by phospholipase $A_2$, hydrolyzing the phospholipid components of the membrane, is believed to be a component in the cellular death resulting from hypoxic states such as coronary infarcts, ligation of the aorta during surgery for aortic aneurysms (resulting in kidney damage), and the like. Inhibition of phospholipase $A_2$ by these compounds could greatly ameliorate the cellular damage resulting from such causes. See Zalewski, et al., Clinical Research 31:227 (1983). This is a preferred use of these compounds.

Asthma is a disease of the lungs in which a wide variety of stimuli can result in an asthmatic attack. These stimuli range from damp cold air to allergens in the environment. The asthmatic response is characterized by constriction of the bronchioles leading to increased airway resistance. There is an early constrictive phase due to histamine release from mast cells, as well as other modulators, e.g., peptides. A late sustained phase then occurs which, in human beings may reach a maximum in 6-8 hours. This phase is slower in onset and disappearance, and is due to a complex of products of the arachidonic acid cascade. These include thromboxanes, prostaglandins, and leukotrienes. The precursor for all of these eicosanoids is arachidonate which is released from esterified forms in membranes to the appropriate enzymes by the action of phospholipase $A_2$. See, e.g., "Corticosteroid Treatment in Allergic Airway Diseases," Proceedings of a Symposium in Copenhagen Oct. 1-2, 1981 (Editors: T. H. Clark, N. Myginfd, and O. Selroos, Munksgaard/Copenhagen 1982). Thus, a block of the phospholipase $A_2$, which is physiologically acceptable, will prevent release of eicosanoids in the lung, thought to be responsible for the "2nd wave" of airway resistance. This is a preferred use of the compounds of this invention.

Increased phospholipase activity has been observed after central nervous system (CNS) trauma, e.g., brain and spinal cord injury. See, E. P. Wei, et al., J. Neurosurg. 56:695-698 (1982) and E. D. Hall and J. M. Braughler, Surgical Neurology 18:320-327 (1982). Thus, phospholipase inhibitors, such as the compounds of the present invention, would be useful in the treatment or prevention of such conditions.

The method of this invention is useful both in treating a phospholipase $A_2$ mediated condition (PMC) or symptoms which has already manifested itself in the mammal as well as the prevention of these conditions or symptoms in mammals including those particularly susceptible to them. Employment of the method of this invention prior to the development of a PMC would prevent the formation of the prostaglandins and similar products necessary for such conditions. Thus, the method of this invention can be used to prevent edema and erythema from sunburn by administering these compounds prior to exposure to sunlight. The compounds of this invention could be administered to persons suffering from hayfever or similar allergies prior to exposure to allergenic substances which are particularly hard on hayfever suffers. In a like manner, a physician or veterinarian could readily determine other mammals or persons susceptible to a PMC.

It is most preferred to use the compounds of this invention in the treatment or prevention of asthma and in the treatment or prevention of cellular death resulting from hypoxic states.

Once a PMC has manifested itself a physician or verterinarian could readily determine the necessity of employing the process of this invention.

The actual inhibition of phospholipase $A_2$ by the method of this invention takes place on a cellular level. Administration of the compound of this invention can thus be by any manner which will allow for phospholipase $A_2$ inhibition in the affected tissues or organs. The preferred route in most cases would be to systemically administer the compounds, i.e., to allow them to enter the mammal's bloodstream and thus be distributed throughout the mammal's system. In certain cases, where the PMC is of a localized nature (e.g., sunburn), topical administration (e.g., transdermal) may be employed in order that the phospholipase $A_2$ inhibition is confined to the afflicted area.

Since the diseases or conditions resulting from the arachidonic acid cascade are varied, methods of administering these compounds must depend on the particular phospholipase mediated condition (PMC) sought to be treated. Regardless of the route of administration selected the compounds used in the process of the present invention are formulated into pharmaceutically acceptable dosage form by conventional methods known to the pharmaceutical art.

Thus, the compounds can be administered orally in forms such as pills, capsules, solutions or suspensions. They may also be administered rectally or vaginally in forms such as suppositories or bougies. They may also be introduced parenterally, e.g., subcutaneously, intravenously, or intramuscularly using sterile injectable forms known to the pharmaceutical art. For treatment of conditions such as erythema the compounds of this invention may also be administered topically in the form of ointments, creams, gels, or the like.

In general the preferred route of administration is oral.

The dosage regimen for preventing or treating phospholipase mediated conditions (PMC) by the compounds of this invention is selected in accordance with a variety of factors., including the type, age, weight, sex and medical condition of the mammal, the severity of the PMC and the particular compound employed. An ordinarily skilled physician or veterinarian will readily determine and prescribe the effective amount of the anti-PMC agent to prevent or arrest the progress of the condition. In so proceeding the physician or veterinarian could employ relatively low dosages at first, subsequently increasing the dose until a desired or maximum response is obtained.

Initial dosages of the compounds of this invention can be from about 0.003 to 4.0 g per 70 kg mammal per 8 hours orally. When other forms of administration are employed, equivalent doses are administered. When dosages beyond 2.0 g per 70 kg mammal per 8 hours are employed, care should be taken with each subsequent dose to monitor possible toxic effects.

Most importantly, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range of 0.01 to 100 $\mu$g per kg per minute until relief from pain is attained. When used for these purposes, these novel compounds cause fewer and less severe undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions, are preferred.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate, methanesulfonate, p-toluenesulfonate, $\beta$-naphthalenesulfonate, fumarate, citrate, and the like. These salts may also be in hydrated or solvated form.

The compounds of the present invention are prepared by the methods depicted in Charts A and B.

In Chart A, $Y_1$, $R_1$, $R_2$, and n are as defined above. The starting 2-aminobenzophenones of the Formula A-1 are well known in the art, particularly because of their usefulness in the preparation of 1,4-benzodiazepine compounds. See for example L. H. Sternbach, Progress in Drug Research, Vol. 22, page 229 (1978). A 2-aminobenzophenone of the Formula A-1 is reacted with an appropriate Grignard reagent, for example, $R_2MgBr$, or with a suitable organolithium reagent, for example $R_2Li$, in a suitable solvent, for example diethyl ether and the like to produce the $R_2$-substituted amino-alcohol of the Formula A-2. The amino-alcohol of the Formula A-2 is chloroacetylated by reaction with chloroacetyl chloride at about 0° to 30° C. in a suitable solvent such as diethyl ether in the presence of a suitable acid scavenger, for example a teritary amine such as triethylamine, to produce an amide of the Formula A-3. An amide of the Formula A-3 is reacted with a suitable base such as sodium hydride in a suitable solvent such as tetrahydrofuran (THF), at about 10° to 30° C. for up to 20 hours and then at the reflux temperature of the mixture for up to four hours to produce a ring-closed 4,1-benzoxazepine-2(3H)-one of the Formula A-4. A Formula A-4 amide is alkylated on nitrogen by reaction with a suitable base such as sodium hydride in a suitable solvent such as dimethylformamide (DMF) for up to three hours at about 10° to 95° C. Lower temperatures are preferred for this reaction when $R_2$ is phenyl. To the reaction mixture thus obtained (after cooling if desired) is added the appropriate alkyl halide of the formula $R_1CH_2CH_2(CH_2)_nCl$ or $R_1CH_2CH_2(CH_2)_nBr$ either without a solvent or in a suitable solvent such as xylene or DMF, and this mixture is then reacted at up to 100° C. for up to 24 hours to produce a compound of this invention of the Formula A-5.

Similarly, in Chart B, $Y_1$, $R_1$, $R_2$ and n are as defined above and Z is either chloro or bromo. The starting 2-aminobenzophenones of the Formula B-1 are well known in the art, particularly because of their usefulness in the preparation of 1,4-benzodiazepine compounds. See for example L. H. Sternbach, Progress in Drug Research, Vol. 22, page 229 (1978). A 2-aminobenzophenone of the Formula B-1 is reacted with an appropriate Grignard reagent, for example, $R_2MgBr$, or with a suitable organolithium reagent, for example $R_2Li$, in a suitable solvent, for example diethyl ether and the like to produce the $R_2$-substituted amino-alcohol of the Formula B-2. The amino-alcohol of the Formula B-2 is chloroacetylated by reaction with chloroacetyl chloride at about 0° to 30° C. in a suitable solvent such as diethyl ether in the presence of a suitable acid scavenger, for example a tertiary amine such as triethylamine, to produce an amide of the Formula B-3. An amide of the Formula B-3 is reacted with a suitable base such as sodium hydride in a suitable solvent such as tetrahydrofuran (THF), at about 10° to 30° C. for up to 20 hours and then at the reflux temperature of the mixture for up to four hours to produce a ring-closed 4,1-benzoxazepine-2(3H)-one of the Formula B-4. A Formula B-4 amide is alkylated on nitrogen by reaction with a suitable base such as sodium hydride in a suitable solvent such as dimethylformamide (DMF) for up to three hours at about 10° to 95° C. Lower temperatures are preferred for this reaction when $R_2$ is phenyl. To the reaction mixture thus obtained (after cooling if desired) is added the appropriate alkyl halide of the formula $R_1Cl$ or $R_1Br$ either without a solvent or in a suitable solvent such as xylene or DMF, and this mixture is then reacted at up to 100° C. for up to 24 hours to produce a compound of this invention of the Formula A-5.

As an alternative for making compounds of the Formula I wherein $R_1$ is —$(CH_2)_n$—$NR_4R_5$ an amide of the Formula B-4 is reacted with a suitable base as described above, and the resulting reaction mixture is reacted with an appropriate alkyl halide of the Formula Z—$(CH_2)_n$—Z, wherein each occurrence of Z is the same or different and is chloride or bromine, to produce a haloalkyl intermediate of the Formula B-6. A haloalkyl compound of the Formula B-6 is reacted with an amine of the Formula $NHR_4R_5$ in a suitable solvent, for example a mixture of chloroform, 2-propanol, and acetonitrile, at a temperature from 25° C. to the reflux temperature of the mixture, for a time sufficient to form the corresponding compound of the Formula B-5. The Formula $HNR_4R_5$ amines are known or can be prepared by known methods.

In compounds of the Formula I carbon atom number five ($C_5$) bears phenyl and $R_2$ as substituents, and when these $C_5$ substituents are different, $C_5$ is thus asymmetrically substituted and can possess either the R- or the S-configuration. Thus these Formula I compounds can exist as the racemate ((+)-form) or as a single enantiomer ((+)- or (−)-form) substantially free of the other enantiomer or as varying mixtures of the enantiomers, and all such stereoisomers are included within the scope of this invention and are meant to be included within the scope of Formula I. The enantiomers of a particular compound are separated by known resolution methods. For example the Formula A-2 amino-tertiary alcohols are separated, i.e. resolved, into their respective optical isomers (enantiomers), as is standard in the isomer resolution art, by reacting the amine moiety with any of the known resolving agents such as optically active camphorsulfonic acid, bis-o-toluoyltartaric acid, tartaric acid, diacetyl tartaric acid, and the like, which are generally commercially available and which are used for the resolution of amines (bases), as for example in Organic Synthesis, Coll. Vol. V, page 932 (1973), resolution of R-(+) and S-(−)-α-phenylethylamine with (−)-tartaric acid. The diastereomeric salts thus produced have different crystallization properties and are separated by conventional means including differential crystallization. On neutralization of each substantially separated diastereomeric salt with base in a suitable solvent, the corresponding optically active enantiomers of the Formula A-2 are obtained, each of which is purified by conventional means. The optically active Formula A-2 compounds are converted to optically active compounds of the Formula A-5 of this invention as described in Chart A, taking care that racemization does not occur.

Certain compounds of the present invention are preferred. Thus, compounds of the Formula I wherein $R_1$ is —OPhX, —OZ, —OH, —OCH$_3$, —OC$_2$H$_5$, phthalimido, —SPhX or PhX; Z is cyclopentyl or cyclohexyl, $R_3$ is hydrogen, methyl or phenyl; n is zero, 1, or 2; and $Y_1$ is in the 7-position are preferred. 1-(3-phenoxypropyl)-7-chloro-1,5-dihydro-5-methyl-5-phenyl-4,1-benzoxazepin-2(3H)-one (Example 2) is most preferred.

DESCRIPTION OF THE PREFERRED EMBODIMENTS

In this specification ether refers to diethyl ether unless otherwise indicated. NaHCO$_3$ means sodium bicarbonate; MgSO$_4$ means magnesium sulfate; the phrase "dried (MgSO$_4$)" generally means that a solution was dried by contacting with anhydrous magnesium sulfate followed by separation, usually filtration, of the liquid from the magnesium containing solids. THF means tetrahydrofuran; NaH means sodium hydride; MeOH means methanol; DMF means N,N-dimethylformamide; HCl means hydrogen chloride; CH$_2$Cl$_2$ means methylene chloride; CHCl$_3$ means chloroform; SSB means Skellysolve B which is a trade name for a solvent which is essentially n-hexane, bp 60°–68° (Merck Index 9th Edition, page 1106).

Preparation 1

2,4'-Dichloro-α-hydroxy-α,α-diphenyl-o-acetotoluidide (2-amino-5-chlorophenyl)diphenylmethanol. Refer to Chart A (conversion of A-1 to A-2).

Phenylmagnesium bromide (267 ml of 3M solution in ether; 0.8 mole) is added during 35 minutes to a solution of 2-amino-5-chlorobenzophenone and the mixture is then refluxed for 4 hours. It is decomposed with 400 ml of water and stirred for 30 minutes. The ether layer is decanted, washed with 200 ml of water, and 200 ml of saturated salt solution, dried (MgSO$_4$) and evaporated. The residue is crystallized from 200 ml of ether and 200 ml of petroleum-ether (30°–60° C.) to give 31 g of yellow rods, mp 127°–128.5° C. The second crop: 15 g, mp 126°–28° C. Yield 73%. The analytical sample melted at 128°–129.5° C. Spectral data support the product structure.

Anal. Calcd. for $C_{19}H_{16}ClNO$: C, 73.66; H, 5.21; Cl, 11.45; N, 4.52.

Found: C, 73.31; H, 5.19; Cl, 11.45; N, 4.71.

This compound was reported in J. Gen. Chem. U.S.S.R. (Eng. Transl) 27, 539 (1957) by the reaction of methyl 5-chloroanthranilate with phenylmagnesium iodide; mp 123.5°–125° C.

(Conversion of A-2 to A-3).

Triethylamine (10.1 g; 0.1 mole) is added to a solution of (2-amino-5-chlorophenyl)diphenylmethanol (15.49 g; 0.05 mole) in 290 ml of ether, the solution is cooled to 5° C. and treated dropwise during one hour with a solution of chloroacetyl chloride (5.65 g; 0.05 mole) in 145 ml of ether keeping the temperature at 5° C. The mixture is then stirred at 5° C. for one hour, and at room temperature for 18 hours. It is cooled in ice, 290 ml of water is added, and the mixture stirred at room temperature for 30 minutes. The suspension is filtered, and the solid washed with water and ether to give 8.15 g of titled dichloro product with melting point of 185°–186.5° C. The filtrate is separated into layers and the aqueous layer is extracted once with ether. The combined ether extract is washed with cold solvents as follows: water (100 ml), 10% hydrogen chloride (3×50 ml), water, NaHCO$_3$ solution (3×50 ml), saturated salt solution. It is dried (MgSO$_4$) and evaporated. Crystallization from ether gives 5.05 g of titled product with a melting point of 184°–185° C. The analytical sample has mp 186°–187° C. Spectral evidence supports the titled product structure.

Anal. Calcd. for $C_{21}H_{17}Cl_2NO_2$: C, 65.29; H, 4.44; Cl, 18.36; N, 3.63.

Found: C, 65.24; H, 4.61; Cl, 18.46; N, 3.60.

Preparation 2

7-Chloro-1,5-dihydro-5,5-diphenyl-4,1-benzoxazepin-2(3H)-one

Refer to Chart A (conversion of A-3 to A-4).

A solution of the dichloro compound of Preparation 1 (88.84 g, 0.230 mole) in 460 ml of THF is added during 15 minutes to a suspension of NaH (19.36 l g, 0.46 moles of 57% dispersion in mineral oil, washed with ether) in 2300 ml of THF. The mixture is stirred at room temperature for 20 hours, and then refluxed for 1.75 hours. It is evaporated, the residue is cooled in ice and stirred with 2 liters of water for 30 minutes (200 ml of ether is added to aid solidification). The suspension is filtered, and the solid washed with water and ether. Crystallization from MeOH gives 48.53 g as prisms with a melting point of 211.5°–212.5° C. Second crop, 11.1 g with a melting point of 197°–198° C. These two different crops are both the titled compound. Spectral evidence supports the titled product structure.

Anal. Calcd. for $C_{21}H_{16}ClNO_2$: C. 72.10; H, 4.61; Cl, 10.13; N, 4.01.

Found: C, 71.95; H, 4.48; Cl, 10.22; N, 4.02.

Preparation 3

7-Chloro-1,5-dihydro-5-methyl-5-phenyl-4,1-benzoxazepin-2(3H)-one

Refer to Chart A.

2-Amino-5-chloro-α-methylbenzhydrol (conversion of A-1 to A-2).

Methylmagnesium bromide (267 ml of 3M ether-solution; 0.8 mole) is added during 45 minutes to a solution of 2-amino-5-chlorobenzophenone (46.3 g; 0.2 mole) in 1 liter of ether. The mixture is refluxed for 5 hours and allowed to stand overnight. It is then cooled in ice and decomposed with 400 ml of water. The ether layer is decanted, washed with saturated salt solution dried (MgSO4) and evaporated. The residue is crystallized from ether-Skellysolve B to give 37.1 g (75% yield), mp 93°–94° C., unchanged on recrystallization. Spectral data support the product structure.

Anal. Calcd. for $C_{14}H_{14}ClNO$: C, 67.88; H, 5.70; Cl, 14.32; N, 5.65.

Found: C, 67.65; H, 5.73; Cl, 14.49; N, 5.46.

This compound was reported in Helv. Chim. Acta, 48, 336 (1965), mp 93°–94° C.

2,4'-Dichloro-2'-(α-hydroxy-α-methylbenzyl)-acetanilide (Conversion of A-2 to A-3).

A solution of chloroacetyl chloride (2.3 g; 0.02 mole) in 50 ml of ether is added during 40 minutes to a solution of 2-amino-5-chloro-α-methylbenzhydrol (4.95 g; 0.02 mole) and triethylamine (4.95 g; 0.02 mole) in 100 ml of ether keeping the temperature at 5° C. The mixture is stirred overnight at room temperature. Water (100 ml) is added at 5° C. and the mixture is stirred at room temperature for 30 minutes. The organic layer is separated, washed with 10% hydrochloric acid (3×20 ml), then with saturated sodium bicarbonate solution (2×50 ml), dried (MgSO4) and concentrated. The residue is crystallizaed from ether to give 4.3 g (66% yield) of colorless needles, mp 161°–162° C. unchanged on recrystallization. Spectral data support the product structure.

Anal. Calcd. for $C_{16}H_{15}Cl_2NO_2$: C, 59.27; H, 4.66; Cl, 21.87; N, 4.32.

Found: C, 59.41; H, 4.54; Cl, 22.04; N, 4.10.

(Conversion of A-3 to A-4).

A solution of 2,4'-dichloro-2'-(α-hydroxy-α-methylbenzyl)acetanilide (73.1 g; 0.23 mole) in 500 ml THF is added to a stirred suspension of sodium hydride (19.8 g, 57% dispersion in mineral oil; 0.48 mole) in 5000 ml THF and the mixture is stirred overnight. The mixture is refluxed for 5 hours and evaporated to near dryness. The residue is treated with 2000 ml cold water, and the resulting precipitate is filtered. Trituration with methanol and ether gives 56.2 g (87% yield) of titled product with a melting point of 219°–222° C. Spectral evidence supports the titled product structure.

Anal. Calcd. for $C_{16}H_{14}ClNO_2$: C, 66.78; H, 4.90; N, 4.87; Cl, 12.32.

Found: C, 67.04; H, 4.76; N, 4.75; Cl, 12.41.

Preparation 4

2-Amino-α-methylbenzhydrol

Refer to Chart B (conversion of B-1 to B-2).

The titled compound is prepared according to the procedure of M. Stiles and A. J. Sisti, J. Org. Chem. 26, 3639 (1961), m.p. 84°–85° C. reported m.p. 84°–85° C.; uv (EtOH) λmax 238, 288; IR yields peaks at 3520, 3460, 3370, 1620, 1600, 1575 1495, 1165, 1070, 760 and 700 cm$^{-1}$; NMR in CDCl3 is in accord; mass spectrum; M+213.

Preparation 5

2-Chloro-2'-(α-hydroxy-α-methylbenzyl)-acetanilide

Refer to Chart B (conversion of B-2 to B-3).

A solution of chloroacetyl chloride (51.6 l g; 0.46 mole) in 1000 ml ether is added with cooling (<10°) to a solution of the compound of Preparation 3 (97.4 g; 0.46 mole) and triethylamine (50.5 g; 0.50 mole) in 2750 ml ether. The mixture is stirred at room temperature overnight and treated with 2500 ml cold water. The ether layer is separated, washed with 10% hydrochloric acid, water, and saturated sodium bicarbonate solution, dried over magnesium sulfate and concentrated to 1000 ml by distillation. On cooling, there is crystallized 67.3 g of the titled product, m.p. 147°–148° C. A second crop is obtained by concentration to 300 ml, 36.5 g, m.p. 146°–147° (78% total yield). uv (EtOH) λmax 205, 246; IR 3410, 3300, 1665, 1605, 1585, 1495, 1525, 1260, 770, 765, and 705; nmr in DMSO-d6 is in accord; mass spectrum: M+, 289; M++2, 291.

Anal. Calcd. for $C_{16}H_{16}ClNO_2$: C, 66.32; H, 5.51; N, 4.84; Cl, 12.24.

Found: C, 66.50; H, 5.49; N, 5.25; Cl, 12.50.

Preparation 6

1,5-Dihydro-5-methyl-5-phenyl-4,1-benzoxazepin-2(3H)-one

Refer to Chart B (conversion of B-3 to B-4)

A solution of the compound of Preparation 5 (98.0 g, 0.34 mole) in 500 ml. THF is added to a stirred suspension of sodium hydride (30.0 g, 57% dispersion in mineral oil; 0.71 mole) in 2000 ml. THF, and the mixture is stirred overnight. The mixture is refluxed for 2 hours and evaporated to near dryness. The residue is treated with 2500 ml water and the resulting precipitate is filtered and washed with Skellysolve B. Recrystallization from methanol gives 64.0 g (74% yield), m.p. 156°–158°; uv (EtOH) λmax 207, 246, 257, 276, and 286; IR 3200, 3160, 3070, 1665; 1605, 1585, 1525, 1495, 1410, 1130, 770, 775, and 705 cm$^{-1}$; nmr in DMSO-d6 is in accord; mass spectrum: M+, 253.

Anal. Calcd. for $C_{16}H_{16}NO_2$: C, 75.86; H, 5.97; N, 5.53.

Found: C, 75.95; H, 6.06; N, 5.61.

Preparation 7

1-(3-Bromopropyl)-7-chloro-1,5-dihydro-5-methyl-5-phenyl-4,1-benzoxazepin-2(3H)-one (Conversion of B-4 to B-6).

A mixture of sodium hydride (1.32 g, 50% mineral oil) and 7.19 g of the compound of Preparation 3 in 100 ml of DMF is heated at 95° C. for 1 hour and then is cooled to 35° C. and 1,3-dibromopropane (4 ml) is added. The mixture is heated at 90° C. for 5 hours, is allowed to stir overnight at 25° C. and is then neutralized with acetic acid and concentrated (using a vacuum pump). The residue is partitioned between methylene chloride and water. The organic extract is filtered through anhydrous sodium sulfate and concentrated. The residue is chromatographed on silica gel and elution with 15–50% ethyl acetate—Skellysolve B gives 3.77 g of crude product as a brown oil which is rechromatographed on silica gel (350 g). Elution (100 ml fractions) with 1–4% acetone-$CH_2Cl_2$ gives 1.79 g of titled product in fractions 20–26 as an oil; $^1$H NMR: 7.8–6.8, 4.1, 3.1, 1.77, 1.4; $^{13}$C NMR: 167.67, 147.23; 141.07, 136.97, 131.83, 129.82, 128.51, 128.26, 127.15, 124.37, 124.02, 80.95, 67.06, 46.64, 31.98, 30.92, 29.94; Anal. Calcd. for $C_{19}H_{19}BrClNO_2$: C, 55.83; H, 4.69; N, 3.43. Found: C, 56.07; H, 4.40; N, 3.52.

This reaction is also carried out in DMSO with dimsyl sodium to give a 33% yield of the titled compound.

EXAMPLE 1

1-(3-Phenoxypropyl)-7-chloro-1,5-dihydro-5,5-diphenyl-4,1-benzoxazepin-2(3H)-one (Formula I: $Y_1$ is 7-chloro, $R_3$ is phenyl, $R_1$ is phenoxy, n is one). Refer to Chart A (conversion of A-4 to A-5).

Sodium hydride (700 mg, 50% mineral oil) is degreased (2×20 ml hexane), dried under vacuum, mixed with 100 ml of dry dimethyl formamide (DMF); 3.5 g of the compound of Preparation 2 is then added. The mixture is stirred for 2 hours at 25° C., then sodium iodide (150 mg) and 3 ml of 3-phenoxypropyl bromide is added. After stirring overnight, the reaction mixture is neutralized with acetic acid and evaporated (vacuum pump). The residue is partitioned (methylene chloride/water), the organic extract filtered through sodium sulfate and evaporated. The residue is chromatographed on 350 g of silica gel packed in 1% acetone-methylene chloride. Elution (100 ml fractions) with 500 ml of 1%, 2% and 3% and 1 liter of 4% acetone-methylene chloride gives 4.4 g (91%) of pure titled product as a white foam in fractions 13–17. $^1$H NMR ($\delta$): 7.6–6.7, 4.35, 3.82, 3.1, 1.9; $^{13}$C NMR ($\delta$); 167.52, 158.60, 144.19, 142.24, 137.60, 131.51, 129.89, 129.50, 128.12, 127.85, 127.40, 124.03, 120.91, 114.53, 86.40, 67.85, 65.33, 46.93 and 27.91.

EXAMPLE 2

1-(3-Phenoxypropyl)-7-chloro-1,5-dihydro-5-methyl-5-phenyl-4,1-benzoxazepin-2(3H)-one (Formula I: $Y_1$ is 7-chloro, $R_3$ is methyl, $R_1$ is phenoxy, n is one). Refer to Chart A (conversion of A-4 to A-5).

A mixture of sodium hydride (2.1 g, 50% mineral oil) and 8.61 g of the compound of Preparation 3 in 120 ml of DMF is stirred at 95° C. for 1 hour and then is cooled to room temperature. Sodium iodide (450 mg) and 3-phenoxypropyl bromide (15 ml) is added and the mixture is stirred overnight at 25° C. The reaction mixture is worked up as in the previous example and the crude product is chromatographed on silica gel. Elution with 1% and 2% methanol-methylene chloride and crystallization of pure fractions from ether gives 3.4 g of titled product. Mother liquors were rechromatographed on silica gel eluting with methanol-methylene chloride or 2% acetone-methylene chloride to give an additional 2.8 g of titled product. A sample of titled product from another run is crystallized from ether; mp 134°–136° C.; $^1$H NMR: 7.6–6.7, 4.1. 3.7, 3.1, 1.77, 1.7$\delta$; $^{13}$C NMR: 167.65, 158.59, 147.29, 141.55, 136.91, 131.67, 129.78, 129.73, 128.21, 127.10, 124.36, 120.83, 114.50, 80.95, 67.22, 65.30, 45.65, 31.92, 27.24 $\delta$. Anal. Calcd. for $C_{25}H_{24}ClNO_3$: C, 71.17; H, 5.73; N, 3.32; Cl, 8.4. Found: C, 71.42; H, 5.70; N, 3.36; Cl, 8.23.

EXAMPLE 3

1-(2-Phenoxyethyl)-7-chloro-1,5-dihydro-5-methyl-5-phenyl-4,1-benzoxazepin-2(3H)-one (Formula I: $Y_1$ is 7-chloro, $R_3$ is methyl, $R_1$ is phenoxy, n is zero) refer to Chart A (conversion of A-4 to A-5).

A 2.87 g sample of the compound of Preparation 3 is allowed to react with 4 g of $\beta$-bromophenetole (2-bromoethyl phenyl ether) essentially as described in Example 2 except that sodium iodide (150 mg) is added to the reaction mixture. The crude product is chromatographed on silica gel. Elution with 2% and 3% methanol-methylene chloride gives 3.29 g (81%) of titled product as a colorless glass; $^1$H NMR ($\delta$): 7.9–6.7, 4.1, 3.5, 3.0, 1.78; $^{13}$C NMR: 167.96, 158.28, 147.42, 141.60, 136.95, 132.10, 129.91, 129.49, 128.25, 128.11, 127.17, 126.27, 124.31, 121.10, 114.44, 80.95, 67.07, 64.61, 48.87, and 31.72 $\delta$.

EXAMPLE 4

1-(4-Phenoxybutyl)-7-chloro-1,5-dihydro-5-methyl-5-phenyl-4,1-benzoxazepin-2(3H)-one (Formula I: (Formula I: $Y_1$ is 7-chloro, $R_3$ is methyl, $R_{1\ L\ is\ phenoxy,\ n\ is}$ 2). Refer to Chart A (conversion of A-4 to A-5).

A 2.87 g sample of the compound of Preparation 3 is allowed to react with 4.6 g of 4-phenoxybutyl-bromide essentially as described above. Chromatography of the crude product on silica gel and elution with 2% and 3% methanol-methylene chloride gives 2.8 g (65%) of titled product as a colorless glass; $^1$H NMR: 7.9–6.8, 4.1, 3.75, 3.05, 1.77, 1.7–0.8 $\delta$; $^{13}$C NMR: 167.34, 158.83, 147.26, 141.29, 137.03, 131.57, 129.64, 129.39, 128.38, 128.15, 126.99, 124.37, 124.08, 120.60, 114.41, 80.90, 67.09, 47.61, 31.92, 26.70 and 24.05 $\delta$.

EXAMPLE 5

1-(3-Phenylpropyl)-7-chloro-1,5-dihydro-5-methyl-5-phenyl-4,1-benzoxazepin-2(3H)-one (Formula I: $Y_1$ is 7-chloro, $R_3$ is methyl, $R_1$ is phenyl, n is one). Refer to Chart A (conversion of A-4 to A-5).

A 2.87 g sample of the compound of Preparation 3 is allowed to react with 3 ml of 1-bromo-3-phenylpropane essentially as described above. Chromatography of the crude product on silica gel and elution with 2% and 3% methanol-methylene chloride gives 3.3 g (85%) of titled product as a colorless glass; $^1$H NMR: 7.8–6.8, 4.1, 3.0, 2.35, 1.72 and 1.4 $\delta$; $^{13}$C NMR: 167.39, 147.19, 141.22, 141.03, 137.09, 131.57, 129.60, 128.23, 127.07, 125.91, 124.39, 123.99, 80.92, 67.19, 47.36, 33.21, 31.92, and 28.53 $\delta$.

EXAMPLE 6

1-(3-Phthalimidopropyl)-7-chloro-1,5-dihydro-5-methyl-5-phenyl-4,1-benzoxazepin-2(3H)-one

(Formula I: $R_1$ is phthalimido, n is 1, $Y_1$ is 7-chloro, $R_3$ is methyl). Refer to Chart A (conversion of A-4 to A-5)

A 2.87 g sample of the compound of Preparation 3 is allowed to react with 4 g of N-(3-bromopropyl)phthalimide essentially as described above. The product obtained by chromatography on silica gel and elution with 3% and 5% methanol —$CH_2Cl_2$ is crystallized twice from acetone-ether to give 1.38 g (29%) of titled product.

M.P. 151°–153° C.; $^1H$ NMR: 8.0–6.7, 4.1, 3.4, 3.0, 1.78, 1.3 δ; $^{13}C$ NMR (δ): 167.96, 167.41, 147.19, 141.10, 137.19, 133.97, 132.07, 131.83, 129.81, 128.44, 128.23, 127.12, 124.35, 123.19, 80.93, 67.06, 53.47, 45.54, 35.66, 31.88, 26.39; Anal. Calcd. for $C_{27}H_{33}ClN_2O_4$: C, 68.28; H, 4.88; N, 5.9; Cl, 7.46; Found: C, 68.32; H, 5.03; N, 5.91; Cl, 7.42.

EXAMPLE 8

7-Chloro-1-(cyclopropylmethyl)-1,5-dihydro-5,5-diphenyl-4,1-benzoxazepin-2(3H)-one

(Formula I: $R_1$ is cyclopropylmethyl, $Y_1$ is 7-chloro, $R_2$ is phenyl). Refer to Chart B (conversion of B-4 to B-5).

The compound of Preparation 2 (3.49 g; 0.01 mole) is added to a suspension of NaH (0.421 1 g, 0.01 mole of 57% dispersion in mineral oil washed with petroleum ether 30°–60° C.) in 100 ml of DMF. After 2 hours the resulting solution is treated during 2 minutes with a solution of (bromomethyl)cyclopropane (2.7 g; 0.02 mole) in 5 ml of DMF, and stirred at room temperature for 23 hours. It is evaporated and the residue is crystallized from ether to give 2.356 g of colorless rods, melting point 147°–148° C. The second crop: 0.72 g with melting point of 136°–148° C. contains some starting material by tlc. The analytical sample melted at 148°–149° C. Spectral evidence supports the titled product structure.

Anal. Calcd. for $C_{25}H_{22}ClNO_2$: C, 74.34; H, 5.49; Cl, 8.78; N, 3.47.

Found: C, 74.45; H, 5.54; Cl, 8.79; N, 3.53.

EXAMPLE 9

7-Chloro-1-(cyclopropylmethyl)-1,5-dihydro-5-methyl-5-phenyl-4,1-benzoxazepin-2(3H)-one

(Formula I: $R_1$ is cyclopropylmethyl, $R_2$ is methyl, $Y_1$ is 7-chloro). Refer to Chart B (conversion of B-4 and B-5)

A mixture of sodium hydride (0.44 g, 57% dispersion in mineral oil; 0.01 mole) and the compound of Preparation 3 (2.87 g; 0.01 mole) in 100 ml DMF is stirred at room temperature for 2 hours. Cyclopropylmethyl bromide (2.70 g; 0.02 mole) is added in one portion, and the mixture kept overnight. The mixture is evaporated at reduced pressure and the residue treated with water and methylene chloride. The organic phase is washed with water and saturated salt solution, dried (MgSO$_4$) and evaporated. The residue is chromatographed on silica gel (200 g) eluting with chloroform in 25 ml fractions. Fractions 1–30 contain no material; fractions 31–79 contain the titled product, recrystallized from ether-petroleum ether (30°–60° C.), 2.0 g (59% yield) with a melting point of 87°–88° C.; succeeding fractions contain the titled product of Preparation 3 (based on tlc). Spectral evidence supports the titled product structure.

Anal. Calcd. for $C_{20}H_{20}ClNO_2$: C, 70.26; H, 5.90 N, 4.09; Cl, 10.37.

Found: C, 69.98; H, 6.01; N, 4.08; Cl, 10.36.

EXAMPLE 10

7-Chloro-1-[2-(dimethylamino)ethyl]-1,5-dihydro-5-methyl-5-phenyl-4,1-benzoxazepin-2(3H)-one and its hydrochloride

(Formula I: $R_1$ is dimethylaminoethyl, $R_2$ is methyl, $Y_1$ is 7-chloro). Refer to Chart B (conversion of B-4 to B-5).

A mixture of sodium hydride (0.67 g, 57% dispersion in mineral oil; 0.016 mole) and the compound of Preparation 3 (4.32 g; 0.015 mole) in 100 DMF is heated at 95° C. for one hour. A solution of 1-chloro-2-(dimethylamino)ethane (3.44 g, 50% solution in xylene; 0.015 mole) (obtained by neutralization of the hydrochloride and distillation) in 50 ml DMF is added dropwise in 20 minutes and heating continued for 5 hours. The mixture is evaporated at reduced pressure and the residue treated with water and methylene chloride. The organic phase is washed with water, 10% HCl, and saturated salt solution, dried (MgSO$_4$), and evaporated. Recrystallization from ethanol-ether gives 3.6 g (61% yield) of the titled product with a melting point of 236°–238° C. Spectral evidence supports the titled product structure.

Anal. Calcd. for $C_{20}H_{23}ClN_2O \cdot HCl$: C, 60.76; H, 6.12; N, 7.09; Cl, 17.94.

Found: C, 60.44; H, 6.15; N, 7.11; Cl, 17.60.

EXAMPLE 11

7-Chloro-1-[3-(dimethylamino)propyl]-1,5-dihydro-5-methyl-5-phenyl-4,1-benzoxazepin-2(3H)-one and its maleate

(Formula I: $R_1$ is 3-(dimethylamino)propyl, $R_2$ is methyl, $Y_1$ is 7-chloro). Refer to Chart B (conversion of B-4 to B-5).

A mixture of sodium hydride (0.67 g, 57% dispersion in mineral oil; 0.016 mole) and the compound of Preparation 3 (4.32 g; 0.015 mole) in 100 ml DMF is heated at 95° C. for 30 minutes. A solution of 1-chloro-3-(dimethylamino)propane (3.22 g, 50% solution in xylene; 0.015 mole) (obtained by neutralization of the hydrochloride and distillation) in 50 ml DMF is added dropwise in 30 minutes and heating continued for 5 hours. The mixture is evaporated at reduced pressure and the residue treated with water and methylene chloride. The organic phase is washed with water and saturated salt solution and extracted with 10% HCl. The aqueous extract is neutralized with 40% sodium hydroxide and extracted with ether. The organic phase is dried (MgSO$_4$) and evaporated to give 3.1 g of the titled free base, a yellow oil (single component by tlc; 9:1 CHCl$_3$:MeOH, silica gel). The oil is treated with maleic acid (1.00 g; 0.0086 mole) in 100 ml ether. Recrystallization gives 3.1 g (42% yield) of titled maleate product with a melting point of 142° C. Spectral evidence supports the titled product structure.

Anal. Calcd. for $C_{21}H_{25}ClN_2O_2 \cdot C_4H_4O_4$: C, 61.41; H, 5.98; N, 5.73; Cl, 7.25.

Found: C, 61.51; H, 6.40; N, 5.86; Cl, 7.24.

EXAMPLE 12

1,5-dihydro-1-[3-(dimethylamino)propyl]-5-methyl-5-phenyl-4,1-Benzoxazepin-2(3H)-one, hydrochloride (Formula I: $R_1$ is -(dimethylamino)propyl, $R_2$ is methyl, $Y_1$ is hydrogen). Refer to Chart B (conversion of B-4 to B-5).

A solution of 2.53 g (10.0 mmol) of the compound of Preparation 6 in 50 ml of dimethylformamide is treated with 0.53 g of 50% sodium hydride in oil (11.0 mmol) until dissolved. The reaction is heated (steam bath) for one hour then cooled slightly. Meanwhile, a solution of 5 g of 3-(dimethylamino)propyl chloride hydrochloride in water is saturated with sodium chloride, covered with ether and made basic with 5% sodium hydroxide solution. The mixture is extracted three times with ether which is washed with saline, dried and carefully evaporated. The residue remaining, 2.77 g (22.8 mmol) is dissolved in 5 ml of dimethyl formamide and added to the hydride reaction. The mixture is stirred well, heated (steam bath) for one hour then allowed to stir at ambient overnight. Further heating does not increase the amount of product (TLC 8% methanol-methylene chloride). Solvent is removed by rota-vac and the residue diluted with water and extracted with methylene chloride. After washing with water, the free amine is converted to the hydrochloride by washing well with 10% hydrochloric acid solution. After washing with saturated saline the solution is dried, evaporated and the residue crystallized from acetone-SSB to give 0.95 g. Chromatography of mother liquors over 10 g of silica gel with 2-10% methanol-methylene chloride gives an additional 0.70 g. Combining and recrystallization from acetone-SSB gives 1.12 g.

Anal. Calcd. for $C_{21}H_{27}N_2O_2Cl.H_2O$: C, 64.19; H, 7.44; N, 7.13; Cl, 9.02.

Found: C, 63.86; H, 7.18; N, 7.05; Cl, 9.60.

IR (thin film) peaks at 3495, 3391, 3074, 3064, 3038, 3013, 2636, 2615, 2520, 2481, 1659, 1642, 1602, 1581, 1497, 1109, 1091, 768, and 702.

Mass spectrum peaks at 338, 280, and 58.

EXAMPLE 13

7-chloro-1,5-dihydro-5-methyl-5-phenyl-1-[3-(1-pyrrolidinyl)propyl]-4,1-benzoxazepin-2(3H)-one, hydrochloride (Formula I: $R_1$ is 3-(1-pyrrolidinyl)propyl, $R_2$ is methyl, $Y_1$ is 7-chloro). Refer to Chart B (conversion of B-6 to B-5).

A mixture of 1.6 g of the compound of Preparation 7 and pyrrolidine (4.5 ml) in chloroform (9.5 ml), 2-propanol (15 ml) and acetonitrile (15 ml) is stirred at 50° C. for 3 days. The mixture is evaporated and the residue partitioned between $CH_2Cl_2$ (30 ml) and 50 ml of water containing 2 ml of 6N HCl.

The aqueous phase is reextracted with $CH_2Cl_2$ (30 ml) and the combined extracts are washed with brine, dried over sodium sulfate and evaporated. The residue is crystallized from ether-methanol to give 1.19 g of a pale brown solid, mp 194°-198° C. Chromatography on silica gel and elution with 20% methanol-$CH_2Cl_2$ does not remove the color.

The column eluates are partitioned between $CH_2Cl_2$ and aqueous HCl as described and the residue is crystallized from methanol-ether to give the titled product; m.p. 196°-198° C.; $^{13}C$ NMR: 167.94, 147.54, 140.75, 136.64, 132.23, 130.27, 128.29, 127.09, 124.94, 124.34, 80.90, 66.87, 53.88, 52.77, 45.36, 31.89, 24.06, 23.32.

Anal. Calcd. for $C_{23}H_{28}Cl_2N_2O_2$: C, 63.44; H, 6.48; N, 6.44; Cl, 16.29. Found: C, 63.31; H, 6.72; N, 6.38; Cl, 16.29.

EXAMPLE 14

7-Chloro-1-[3-(dimethylamino)propyl]-1,5-dihydro-5,5-diphenyl-4,1-benzoxazepin-2(3H)-one (Formula I: $R_1$ is 3-(dimethylamino)propyl, $R_2$ is phenyl, $Y_1$ is 7-chloro).

Refer to Chart B (conversion of B-4 to B-5).

Sodium hydride (0.421 g; 0.01 mole of 57% dispersion in mineral oil) is added to a solution of the compound of Preparation 2 (3.49 g; 0.01 mole) in 100 ml of DMF and the mixture is stirred for 2.5 hours. The resulting solution is treated with a solution of 3-(dimethylamino)propyl chloride (2.42 g, 0.02 mole, two equivalents) in 2.42 g of xylene and the mixture is heated at 95° C. for 23 hours. It is evaporated and the residue taken up in 100 ml each of water and $CH_2Cl_2$. The organic layer is dried ($MgSO_4$) and evaporated. The residue (3 g) is chromatographed on 300 g of silica gel using $CHCl_3$ (1% $Et_3N$). Fractions 1-90 (25 ml each) give no material. With 1% MeOH—$CHCl_3$ (1% $Et_3N$) fractions 91-137 give no material. Fractions 138-152 give (0.335 g (single spot) that is crystallized from MeOH to give 0.128 g of starting material, m.p. 209°-210° C. Fractions 153-165 give 0.318 g (two spots) which is crystallized from ether to give 22 mg of starting material.

With 2% MeOH—$CHCl_3$ (1% $Et_3N$) fractions 181-223 give no material. Fractions 224-249 give 1.601 g (2 spots) which is crystallized from ether (save filtrate) to give 0.501 g of titled product; m.p. 134.5°-137° C. raised to 138°-139° C. on recrystallization, uv $\lambda$max 204, 253, 257, 264, 271. IR 3060, 2780, 2760, 2720, 1645, 1595, 1565, 1485, 1415, 1170, 1100, 1080, 820, 750 and 700 $cm^{-1}$. NMR in $CDCl_3$ and 100 MHz is in accord.

EXAMPLE 15

7-Chloro-1-[2-(dimethylamino)ethyl]-1,5-dihydro-5,5-diphenyl-4,1-benzoxazepin-2(3H)-one hydrochloride (Formula I: $R_1$ is 2-(dimethylamino)ethyl, $R_2$ is phenyl, $Y_1$ is 7-chloro). Refer to Chart B (conversion of B-4 to B-5).

Sodium hydride (0.421 g; 0.01 mole of 57% dispersion in mineral oil; washed with petroleum-ether 30°-60° C.) is added to a solution of the compound of Preparation 2 (3.49 g; 0.01 mole) in 100 ml of DMF, and the mixture is stirred for 2.5 hr. The resulting solution is treated with a solution of 2-(dimethylamino)ethyl chloride (1.07 g; 0.01 mole) in xylene and heated at 95° for 19 hr. It was evaporated and the residue taken up in 25 ml of water and 50 ml of $CH_2Cl_2$. The aqueous layer is extracted once with $CH_2Cl_2$. Extraction of the $CH_2Cl_2$ solution with 10% of HCl caused a distribution of the hydrochloride between the organic and the aqueous layers. Therefore, a solution of the product as the free base (4.05 g) in 10 ml of $CHCl_3$ is chromatographed on 405 g silica gel using 2% MeOH—$CHCl_3$ (1% $Et_3N$). Fractions 1-10 (925 ml total) gives some mineral oil. Fractions 11-12 (25 ml from now on) give 0.361 g of starting material. Fractions 14-17 (2.68 g) give the desired product which is converted to the hydrochloride in ether with ethereal HCl. Crystallization from MeOH-ether gives colorless needles: 1.832 g, m.p. 260°-261° C. The analytical sample melts at 261°-262° C. UV $\lambda$max 253, 257, 264, 271; IR 3270, 2560, 2380, 1685, 1595, 1565, 1485, 1445, 1420, 1320, 1150, 885, 795, 765, 755 and 705. NMR in $d_6$DMSO indicates some enolic form to be present. Mass spectrum peak at 420.

Anal. Calcd. for $C_{25}H_{25}ClN_2O_2 \cdot HCl$: C, 65.65; H, 5.73; Cl, 15.50; N, 6.13. Found: C, 65.46; H, 5.93; Cl, 15.37; N, 5.85.

EXAMPLE 16

Following the procedures of the preceding Examples, and using the appropriate starting materials, all of the other compounds within the scope of this application are prepared.

FORMULA

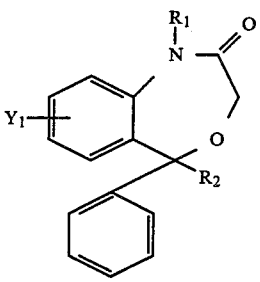

I

CHART A

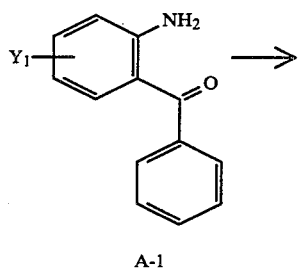

A-1

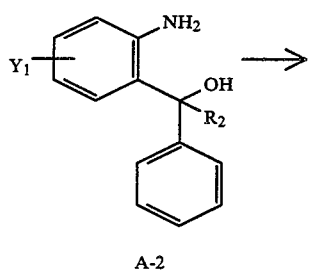

A-2

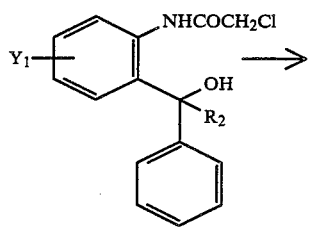

A-3

-continued
CHART A

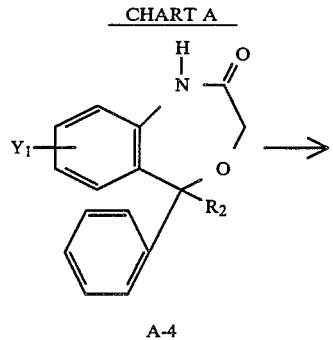

A-4

A-5

CHART B

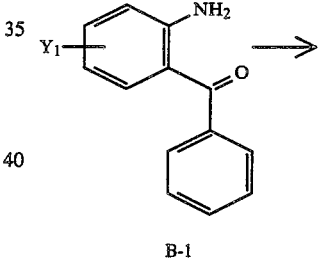

B-1

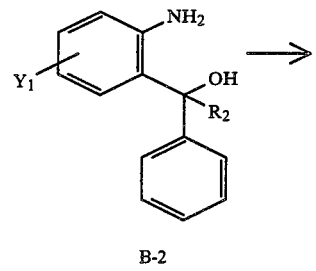

B-2

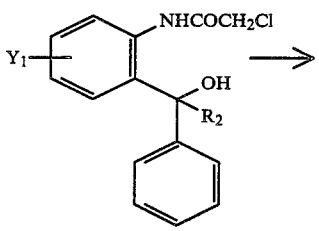

B-3

-continued
CHART B

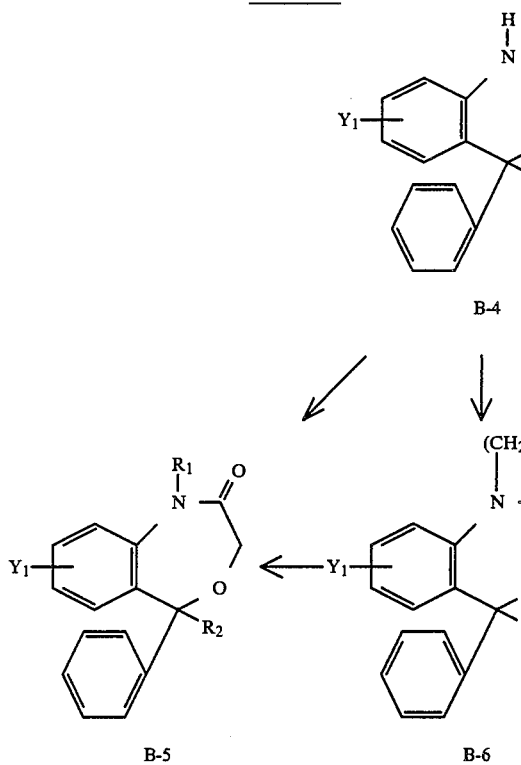

We claim:
1. A compound of the Formula I

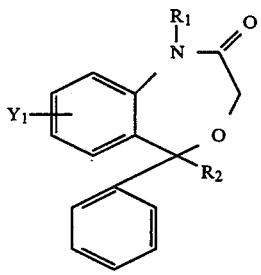

wherein $R_1$ is
(a) cyclopropylmethyl,
(b) 2-phenylethyl,
(c) —$(CH_2)_n$—$NR_4R_5$, or
(d) —$CH_2$—$CH_2$—$(CH_2)_m$—$R_{11}$,
wherein $R_{11}$ is
(a) —O—PhX,
(b) —$S(O)_n$—PhX,
(c) —O—Z,
(d) —PhX,
(e) —$OR_2$, or
(f) phthalimido;
wherein PhX is
(a) phenyl, or
(b) phenyl substituted by $X_1$;
wherein $X_1$ is
(a) chloro
(b) bromo
(c) fluoro,
(d) nitro,
(e) trifluoromethyl, (f) methoxy,
(g) hydroxy,
(h) $(C_1-C_3)$alkyl,
(i) —$SCH_3$, or
(j) —$CO_2M$, wherein M is hydrogen, $(C_1-C_3)$alkyl, or a pharmacologically acceptable cation;
wherein n is 2 or 3, wherein m is an integer from zero to 4, inclusive, with the proviso that m is not zero when $R_{11}$ is phenyl; wherein p is an integer from zero to 2, inclusive, and wherein $R_4$ and $R_5$ are the same or different and are $(C_1-C_3)$alkyl or $R_4$ and $R_5$ together with the nitrogen atom to which they are attached from 1-azetidinyl, 1-pyrrolidinyl, 1-piperidinyl, or 4-morpholinyl; wherein $R_2$ is
(a) hydrogen,
(b) $(C_1-C_3)$alkyl,
(c) phenyl;
wherein Z is $(C_3-C_6)$cycloalkyl; wherein $Y_1$ is
(a) hydrogen,
(b) chloro,
(c) bromo,
(d) fluoro,
(e) nitro, or
(f) trifluoromethyl,
including the acid addition salts thereof when $R_1$ is —$(CH_2)_n$—$NR_4R_5$; with the following provisos:
(1) when $R_1$ is cyclopropylmethyl and $R_2$ is methyl or when $R_1$ is —$CH_2$—$CH_2$—$(CH_2)_m$—$R_{11}$, $Y_1$ is not hydrogen,
(2) when $R_1$ is cyclopropylmethyl, 2-phenylethyl, or —$(CH_2)_n$—$NR_4R_5$, $Y_1$ is not nitro, and
(3) $R_2$ is hydrogen or $(C_2-C_3)$alkyl only when $R_1$ is —$CH_2$—$CH_2$—$(CH_2)_m$—$R_{11}$.
2. A compound of claim 1, wherein $R_1$ is cyclopropylmethyl or 2-(dimethylamino)ethyl; and $Y_1$ is 7-chloro.
3. A compound of claim 2 selected from the group consisting of:
7-chloro-1-(cyclopropylmethyl)-1,5-dihydro-5,5-diphenyl-4,1-benzoxazepin-2(3H)-one,
7-chloro-1-(cyclopropylmethyl)-1,5-dihydro-5-methyl-5-phenyl-4,1-benzoxazepin-2(3H)-one,
7-chloro-1-[2-(dimethylamino)ethyl]-1,5-dihydro-5-methyl-5-phenyl-4,1-benzoxazepin-2(3H)-one and its hydrochloride, and
7-chloro-1-[2-(dimethylamino)ethyl]-1,5-dihydro-5,5-diphenyl-4,1-benzoxazepin-2(3H)-one.
4. A compound of claim 1 wherein $R_1$ is 3-(dimethylamino)propyl and $Y_1$ is hydrogen or 7-chloro.
5. A compound of claim 4 selected from the group consisting of:
7-chloro-1-[3-(dimethylamino)propyol]-1,5-dihydro-5-methyl-5-phenyl-4,1-benzoxazepin-2(3H)-one and its maleate,
1,5-dihydro-1-[3-(dimethylamino)propyl]-5-methyl-5-phenyl-4,1-benzoxazepin-2(3H)-one, and its hydrochloride, and
7-chloro-1-[3-(dimethylamino)propyl]-1,5-dihydro-5,5-diphenyl-4,1-benzoxazepin-2(3H)-one.
6. A compound of claim 1, wherein $R_1$ is —$(CH_2)_n$—$NR_4R_5$; $R_4$ and $R_5$ form 1-pyrrolidinyl, and $Y_1$ is 7-chloro.
7. 7-Chloro-1,5-dihydro-5-methyl-5-phenyl-1-[3-(1-pyrrolidinyl)propyl]-4,1-benzoxazepin-2(3H)-one, and its hydrochloride compounds of claim 7.
8. A compound of claim 1, wherein $R_1$ is —$CH_2$—$CH_2$—$(CH_2)_m$—$R_{11}$, $R_{11}$ is —O—PhX, —OZ, —OH, —$OCH_3$, —$OC_2H_5$, phthalimido, —SPhX, or PhX; Z is cyclopentyl or cyclohexyl; $R_3$ is hydrogen, methyl, or phenyl; m is zero, 1, or 2; $Y_1$ is in the 7-position.

9. A compound of claim 8 selected from the group consisting of:
   1-(3-phenoxypropyl)-7-chloro-1,5-dihydro-5,5-diphenyl-4,1-benzoxazepin-2(3H)-one,
   1-(3-phenoxypropyl)-7-chloro-1,5-dihydro-5-methyl-5-phenyl-4,1-benzoxazepin-2(3H)-one,
   1-(2-phenoxyethyl)-7-chloro-1,5-dihydro-5-methyl-5-phenyl-4,1-benzoxazepin-2(3H)-one,
   1-(4-phenoxybutyl)-7-chloro-1,5-dihydro-5-methyl-5-phenyl-4,1-benzoxazepin-2(3H)-one,
   1-(3-phenylpropyl)-7-chloro-1,5-dihydro-5-methyl-5-phenyl-4,1-benzoxazepin-2(3H)-one, and
   1-(3-phthalimidopropyl)-7-chloro-1,5-dihydro-5-methyl-5-phenyl-4,1-benzoxazepin-2(3H)-one.

10. A method for treating or preventing phospholipase $A_2$-mediated conditions (PMC) in a mammal susceptible to said PMC which comprises:
   administering to said mammal an amount effective to inhibit phospholipase $A_2$ of a compound of claim 1.

* * * * *

UNITED STATES PATENT OFFICE
CERTIFICATE OF CORRECTION

Patent No. 4,590,187    Dated 20 May 1986

Inventor(s)    Donald P. Wallach

It is certified that error appears in the above-identified patent and that said Letters Patent are hereby corrected as shown below:

Column 21, line 55: "(b) $-S(O)_n-PhX$" should read -- (b) $-S(O)_p-PhX$ --.

Signed and Sealed this

Fifteenth Day of September, 1987

*Attest:*

DONALD J. QUIGG

*Attesting Officer*    *Commissioner of Patents and Trademarks*